(12) United States Patent
Miller

(10) Patent No.: US 12,329,675 B1
(45) Date of Patent: Jun. 17, 2025

(54) URINE COLLECTION DEVICE

(71) Applicant: Ronald L. Miller, Portland, OR (US)

(72) Inventor: Ronald L. Miller, Portland, OR (US)

( * ) Notice: Subject to any disclaimer, the term of this patent is extended or adjusted under 35 U.S.C. 154(b) by 0 days.

(21) Appl. No.: 19/040,783

(22) Filed: Jan. 29, 2025

(51) Int. Cl.
*A61F 5/449* (2006.01)
*A61F 5/44* (2006.01)
*A61F 5/443* (2006.01)

(52) U.S. Cl.
CPC ............ *A61F 5/449* (2013.01); *A61F 5/4405* (2013.01); *A61F 5/443* (2013.01)

(58) Field of Classification Search
CPC ......... A61F 5/449; A61F 5/4405; A61F 5/443
See application file for complete search history.

(56) References Cited

U.S. PATENT DOCUMENTS

| | | | | |
|---|---|---|---|---|
| 4,096,853 A * | 6/1978 | Weigand | ............... | A61M 25/02 600/431 |
| 4,250,882 A * | 2/1981 | Adair | .................... | A61M 27/00 604/355 |
| 4,533,349 A * | 8/1985 | Bark | ...................... | A61M 25/02 604/174 |
| 5,738,661 A * | 4/1998 | Larice | ...................... | A61J 1/10 604/277 |
| 5,833,666 A * | 11/1998 | Davis | .................... | A61M 25/02 128/DIG. 26 |
| 5,935,115 A * | 8/1999 | Espina | .................... | A61F 5/445 604/277 |
| 9,867,969 B2 * | 1/2018 | Ward | .................... | A61M 25/02 |
| 10,449,083 B2 * | 10/2019 | Pierson | ................. | A61F 5/4404 |
| 10,456,289 B2 * | 10/2019 | Alden | ................... | A61M 25/02 |
| 11,191,662 B2 * | 12/2021 | Cesa | ...................... | A61F 5/4408 |
| 12,083,291 B2 * | 9/2024 | Molina | .................. | A61B 5/031 |
| 2010/0022975 A1 * | 1/2010 | Vanden Bosch | ........ | A61F 5/445 604/338 |

(Continued)

FOREIGN PATENT DOCUMENTS

| | | |
|---|---|---|
| GB | 2531554 A | 4/2016 |
| WO | WO2009068666 A2 | 6/2009 |

OTHER PUBLICATIONS

Bladder Cancer Advocacy Network, "Learning About Ileal Conduits and Common Issues," 5 pages, https://bcan.org/wp-content/uploads/2019/12/Learning-about-Ileal-Conduits-and-Common-Issues.pdf, downloaded Jan. 23, 2025.

(Continued)

*Primary Examiner* — Guy K Townsend
(74) *Attorney, Agent, or Firm* — Klarquist Sparkman, LLP

(57) ABSTRACT

A urine collection device comprises a primary collection element shaped to surround a stoma formed in a person's abdomen, an outlet opening in the primary collection element, a drain tube connected to the outlet opening and extending distally from the primary collection element, an anti-backflow device positioned at the outlet opening of the primary collection element or within the primary collection element, the anti-backflow device restricting urine from backflowing from the drain tube into the primary collection element, and a secondary collection element connected to the distal end of the drain tube to collect the urine draining from the drain tube, wherein the secondary collection element is configured for coupling to the person at a location spaced apart from the primary collection element.

20 Claims, 7 Drawing Sheets

(56) References Cited

U.S. PATENT DOCUMENTS

| | | | | |
|---|---|---|---|---|
| 2010/0042061 | A1* | 2/2010 | Smith | A61F 5/445 |
| | | | | 604/335 |
| 2011/0270187 | A1* | 11/2011 | Nelson | A61M 39/0208 |
| | | | | 604/151 |
| 2014/0213995 | A1* | 7/2014 | Garrettson | A61F 5/442 |
| | | | | 604/344 |
| 2016/0287428 | A1* | 10/2016 | Eggert | A61F 5/445 |
| 2019/0060105 | A1* | 2/2019 | Cesa | A61F 5/4405 |
| 2020/0046543 | A1* | 2/2020 | Scalise | A61F 5/445 |
| 2021/0369492 | A1* | 12/2021 | O'Grady | A61M 39/0247 |
| 2023/0149203 | A1* | 5/2023 | Mandhani | A61F 5/445 |
| | | | | 604/335 |

OTHER PUBLICATIONS

ConvaTec, "Esteem® + Urostomy Pouch with Accuseal® Tap," https://www.convatec.com/products/ostomy-care/surgery-type/ostomy-urostomy/61544738-b1d0-469a-a353-4e9d542f03d4/ (downloaded Jan. 23, 2025).

Johansson, Martin L. et al., "Achieving stomal continence with an iLeal pouch and a percutaneous implant," *Journal of Materials Science: Materials in Medicine*, 33(7) 14 pages (Jan. 4, 2022).

* cited by examiner

URINE COLLECTION DEVICE

BACKGROUND

After a bladder removal surgery (cystectomy ileal conduit), a stoma, that allows urine to freely drain from the kidneys, typically projects from the side of the abdomen at the approximate height, or slightly below the height, of the navel.

One commonly used urine collection system to collect urine from a stoma includes a flexible plastic bag or pouch with an opening in a flange that is placed over and around the stoma and is adhered to the skin to form a sealed connection. This bag arrangement is manufactured by many companies, such as Hollister Inc. and Coloplast.

Typically, the flange is integral with the collection pouch and includes an applied adhesive. The adhesive on the flange is protected with a paper or plastic cover. For use, the protective cover is removed to expose the adhesive.

Some conventional collection systems include a separate flange base for connection with a separate collection pouch. Similar to the integral pouch assembly, the separate flange base is attached around and over the stoma with adhesive. The separate collection pouch then attaches to the separate flange base with a removable interlocking mechanical or friction-type seal (similar to a self-sealing plastic bag).

Conventional collection system pouches can have a drainage spout with a normally closed valve that can be opened to drain urine from the collection bag into a toilet, a urinal or a drain.

A length of separate drainage tubing can be attached to the drainage spout valve. The drainage tube can be routed and connected to a separate container (referred to as a "night bag") that provides greater capacity than the collection pouch alone.

While most of the collection pouches are a single compartment, some urine collection pouch assemblies are divided into two sections with the secondary portion integrated with, but separated from, the primary collection bag. This design typically provides an anti-reflux system between the upper and lower pouches that is claimed to reduce the backflow of urine (at least within the pouch itself). This arrangement may prevent the backflow of urine in some cases but once the lower pouch is full, the anti-reflux system no longer operates and urine then collects in the upper pouch without any protection against backflow. This also increases the chance that the adhesive attaching the pouch to the user weakens and fails because of the additional pressure applied to the upper pouch.

One of the typical issues for a user wearing pants or a garment with a tight waist band or belt is that the collection pouch needs to be worn outside of the belt or waist band. If it is worn inside the belt or waist band, then the pouch's usable volume is effectively restricted to the section above the belt or waist band. With any pressure or deformation of the urine-filled upper part of the collection pouch, the adhesive on the flange holding the pouch to the skin can be compromised, allowing urine to leak from the base of the pouch.

In addition, if unsupported outside of the belt line, the weight of the pouch as it becomes full of urine will affect the performance of the adhesive attachment to the skin, especially while exercising or performing other physical activities.

Without a protective belt-type cover, wearing a garment such as a swimsuit exposes the entire collection pouch.

Along with the packaging and protective paper over the flange adhesive, once the adhesive starts to fail, the entire collection pouch assembly and base is discarded after four to seven days use. This non-compostable paper and plastic is considered medical waste and typically goes to a landfill or in some jurisdictions, requires special disposal, which consumes additional resources.

SUMMARY

Described below are implementations of a urine collection device that addresses some of the problems in the prior art.

According to one implementation, a urine collection device for a person comprises a primary collection element, a drain tube, an anti-backflow device and a secondary collection device. The primary collection element is shaped to surround a stoma formed in the person's abdomen and comprises an outlet opening via which urine received in the primary collection element through the stoma exits the primary collection element. The drain tube is connected to the outlet opening in the primary collection element and extends distally from the primary collection element, draining urine from the primary collection element. The anti-backflow device is positioned at the outlet opening of the primary collection element or within the primary collection element. The anti-backflow device restricts urine from backflowing from the drain tube into the primary collection element. The secondary collection element is connected to the distal end of the drain tube to collect the urine draining from the drain tube. The secondary collection element is configured for coupling to the person at a location spaced apart from the primary collection element.

The secondary collection element can be configured for coupling to the person below a beltline of the person.

The outlet opening in the primary collection element can comprise a protruding spout.

The anti-backflow device can be positioned in the primary collection element, such as in the outlet opening of the primary collection element or elsewhere within the primary collection element. The anti-backflow device can be a check valve installed in the primary collection element with the check valve protruding through the outlet opening and having a barb fitting connected to the drain tube.

The anti-backflow device can comprise a Luer fitting.

The anti-backflow device can comprise a duckbill-type member formed of a flexible material.

The primary collection element can be configured to be adhesively coupled to the person's skin.

The secondary collection element can be shaped to be suspended from a belt worn by the person, the belt being fitted for wearing adjacent the beltline. The secondary collection element can be configured for being received in a pouch of a garment worn by the person. The secondary collection element can be configured for being coupled to a leg of the person.

According to another implementation, a urine collection device for a person, comprises a primary collection element, an anti-backflow device, a drain tube and a secondary collection element. The primary collection element is shaped to surround a stoma formed in the person's abdomen. The primary collection element has a base, a wall extending from the base and a primary collection volume defined by at least the base and the wall. The device comprises a flange that extends outwardly from the base and is configured for adhesive attachment to the person's skin. The primary collection element is configured to receive urine from the body opening into the primary collection volume and convey the urine out of the primary collection volume in a first flow direction through an outlet opening in the wall. The anti-backflow device is positioned at the outlet opening in the wall or within the primary collection element. The drain tube is connected to the outlet opening in the primary collection element and extends distally from the primary collection element, the drain tube having a working length that extends at least as long as a distance from the body opening in the person's abdomen to a desired secondary collection element location below the person's beltline. The secondary collection element is connected to the distal end of the drain tube to collect the urine draining from the drain tube. The secondary collection member is configured for coupling to the person at the desired collection member location. The anti-backflow device is configured to restrict urine from backflowing into the primary collection volume in a second flow direction opposite the first flow direction and compromising the adhesive attachment between the flange and the person's skin.

The drain tube can be sized for wearing under a belt or clothing waist band without being compressed by the belt or clothing waist band. The drain tube can be friction-fitted to a distal end of the anti-backflow device.

DETAILED DESCRIPTION

Described below are implementations of a urine collection device having a primary collection element, an anti-backflow device positioned at or within the primary collection element, a drain tube extending away from the primary collection element and a secondary collection element connected to a distal end of the drain tube.

Figure 1:
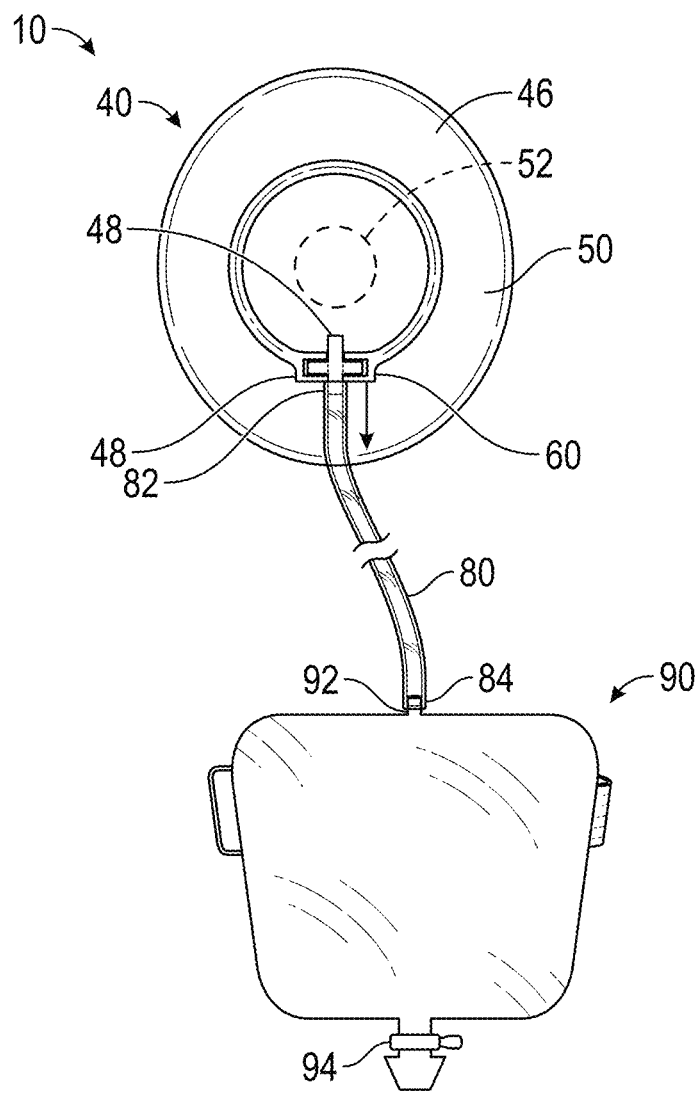
FIG. 1 is a front elevation view of a urine collection device having a primary collection element connected to a secondary collection element via a drain tube.

Referring to FIG. 1, a first implementation of the urine collection device 10 has a primary collection element 40, an anti-backflow device 60, a drain tube 80 and a secondary collection device 90 connected at the distal end of the drain tube 80.

Figure 2:
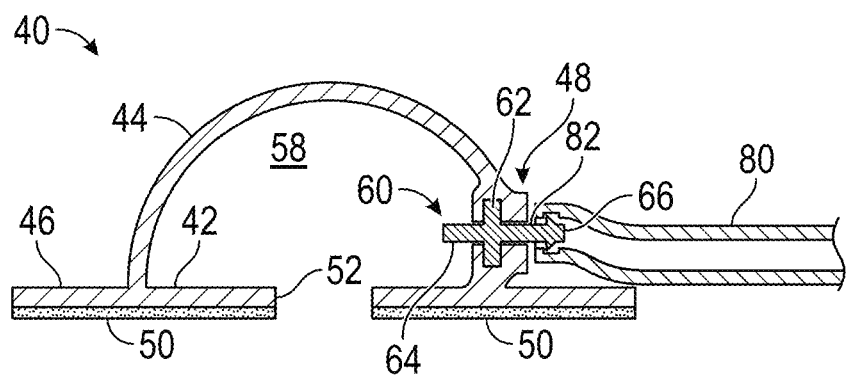
FIG. 2 is a side elevation section view of the primary collection element of FIG. 1.

The primary collection element 40 is shaped to surround the stoma or body opening, which is generally located in the patient's midsection. As shown in FIG. 2, the primary collection element 40 has a base 42 and at least one wall 44 that extends away from the base 42. The base 42 and the wall 44 together define a primary collection volume 58. The primary collection volume 58/wall 44 may have a curved outer profile (dome shape) as shown in FIG. 2, a flat outer profile, or another different shape.

Figure 3:
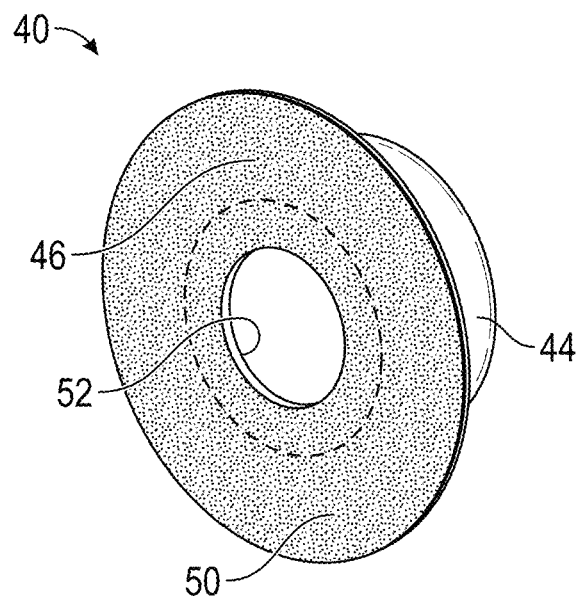
FIG. 3 is a rear perspective view of the primary collection element of FIG. 1.

Referring to FIG. 3, which shows a rear side of the primary collection element 40, there is an orifice 52 formed in the base 42 and shaped to encircle the stoma or body opening. Further, the base may be adjoined by a flange 46 as shown, such as for coupling the primary collection element 40 to the patient. When the urine collection device 10 is worn by the patient, urine is received into the primary collection element 40 via the orifice 50 from the stoma or body opening and initially collects in the primary collection volume 58.

In some embodiments, the primary collection element 40 is coupled to patient using an adhesive 50 between the flange 46 and the patient's skin.

The primary collection element 40 has an outlet opening 48, and the drain tube 80 is connected to the outlet opening 48 (directly or indirectly) to drain urine from the primary collection element 40 to the secondary collection element 90.

The urine collection device 10 preferably has an anti-backflow device 60 that is positioned at, or within, or very close to, the primary collection element 40. The anti-backflow device 60 functions to permit relatively unrestricted flow of urine out of the primary collection element 40 and through the drain tube 80 distally (i.e., away from the primary collection element 40), but blocks or at least substantially restricts flow in an opposite proximal direction (i.e., towards the primary collection element 40). The anti-backflow device is also known as a one-way valve or a check valve. In this way, the anti-backflow device 60 prevents urine in the tube 80 and/or the secondary collection element 90 from backing up into the primary collection element 40, which would increase pressure in the primary collection element 40 and could weaken the adhesive bond between the primary collection element 40 and user's skin (resulting in leaking of urine) and/or impeding the flow of urine from the stoma. The tendency of urine in the drain tube 80 and/or the secondary collection element 90 to backflow toward the primary collection element 40 can be caused by movement, e.g., such as to a sitting or laying position, or another action that exerts pressure on and/or deforms the drain tube and/or the secondary collection element, such as contact with an object.

Referring to FIG. 2, the anti-backflow device has a body 62 with a first end 64 and a second end 66, with the second end being positioned downstream of the first end 64 in the flow direction.

The outlet opening 48 in the wall 44 of the primary collection element 40 can be shaped to receive at least a portion of the body 62 of the anti-backflow device 60. FIG.

Figure 5:
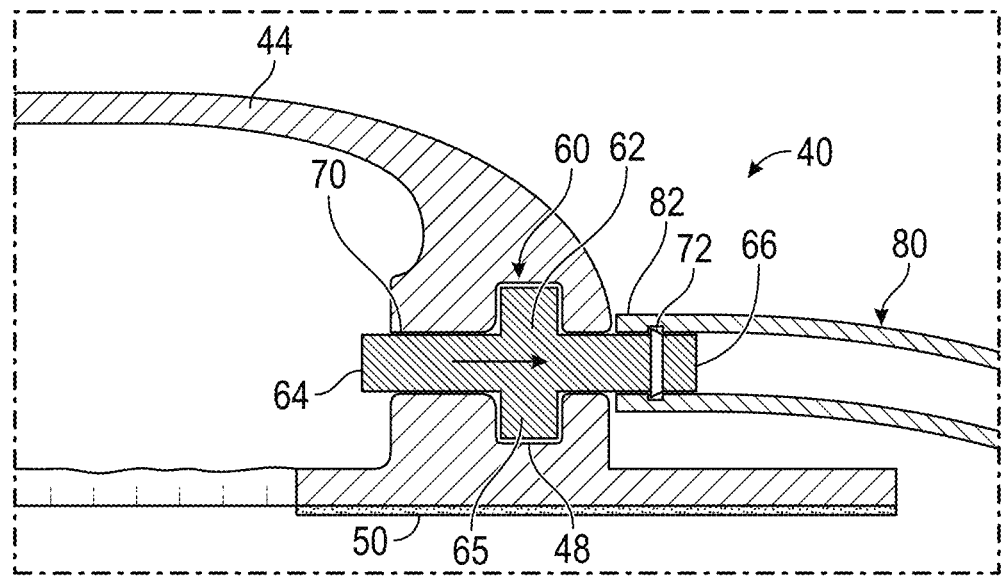
FIG. 5 is an enlarged section view showing the anti-backflow device coupled to the primary collection element.

4 shows the primary collection element 40 without the anti-backflow device 60 installed to illustrate the shape of the outlet opening 48. Additionally, it is also possible to arrange some or all of the anti-backflow device 60 to protrude from the primary collection element 40 (FIGS. 2 and 5). Alternatively, the anti-backflow device 60 can be positioned interiorly of the wall 44, i.e., within the primary collection volume 58.

Figure 4:
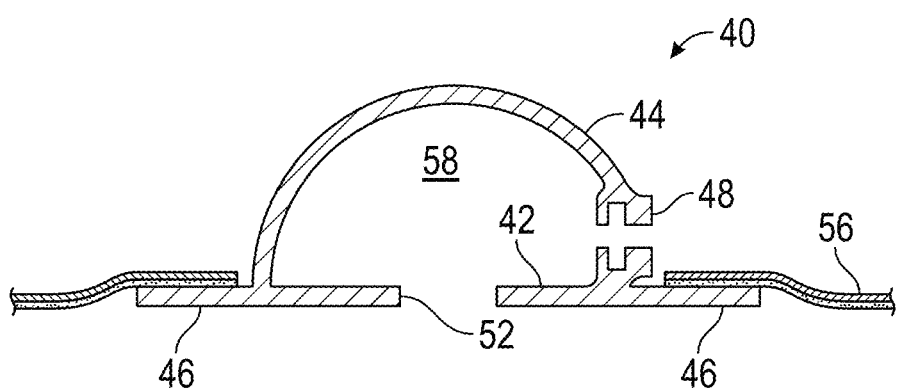
FIG. 4 is a side elevation section view showing an alternative adhesive mounting for the primary collection element.

Referring to FIG. 4, the primary collection element 40 is shown in greater detail. The body 62 of the anti-backflow device 60 is formed with a midsection 65 having a greater dimension than the first end 64 or the second end 66. The body 62 is shown in its installed position within the outlet opening 48 with the second end 66 protruding outwardly beyond the wall 44. The anti-backflow device 60 can be formed in the installed position as shown with the primary collection element 40, or it can be a separate component that is inserted into the primary collection element 40. For example, if the primary collection element 40 is formed of silicone or a similar resilient material, then it can be stretched as the anti-backflow device 60 is inserted into the installed position.

In the illustrated implementation, the anti-backflow device 60 forms part of the connection to the drain tube 80. Specifically, a first end 82 of the drain tube 80 is fitted to an exterior of the second end 66 of the anti-backflow device 60. The second end 66 may be sized and/or shaped to provide an appropriate friction fit that tends to prevent leakage and also retains the drain tube 80 in a connected state over the useful life of the device. For example, the second end 66 may define a Luer fitting (e.g., a slight taper) for establishing an appropriate connection with the drain tube 80.

Alternatively, as shown in FIG. 5, the second end 66 can include a barb fitting 72 to improve the connection to the to the drain tube 80. The first end 64 can also include a barb fitting 72. Instead of or in addition to the barb fitting 72, the second end 66 could be formed with one or more ribs to create a rib fitting.

Figure 6:
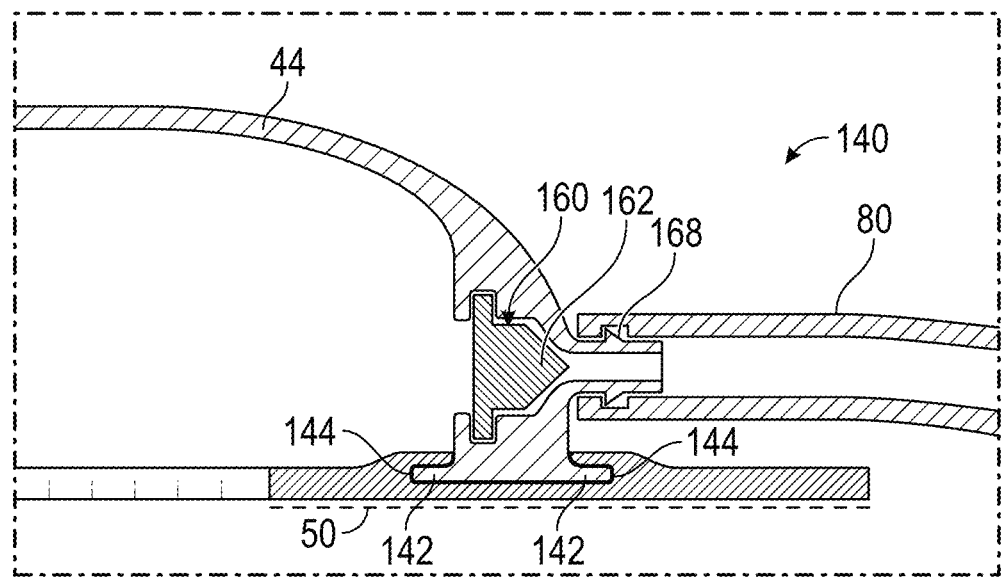
FIG. 6 is a side section view of an alternative primary collection element having a cover that is removably mounted to a base.

As another alternative, an anti-backflow device 160 in the form of a duckbill device as shown in FIG. 6 can be used. As also shown in FIG. 6, a primary collection element 140 is formed with a projecting extension or spout 168, and the drain tube 80 is connected to the spout 168. The spout 168 may have a barb connection as shown, or a friction-fit, Luer, rib or other type of connection can be used.

Suitable anti-backflow devices include the Nordson check valve SCV 06265, with a barb, Luer or other fitting, available from Nordson Medical. Also, suitable medical grade duckbill-type check valves are available from Vernay (www.vernay.com).

In the primary collection element 140 of FIG. 6, the dome-shaped portion (defined by the wall 40) is removably secured to the base, such as by an interlocking seal formed by a mating insert 142 inserted into a mating groove 144 or another suitable resealable connection. Among other benefits, the resealable connection allows for disposing of the base that has the adhesive when it is damaged or no longer usable and reusing the dome-shaped portion.

Figure 7:
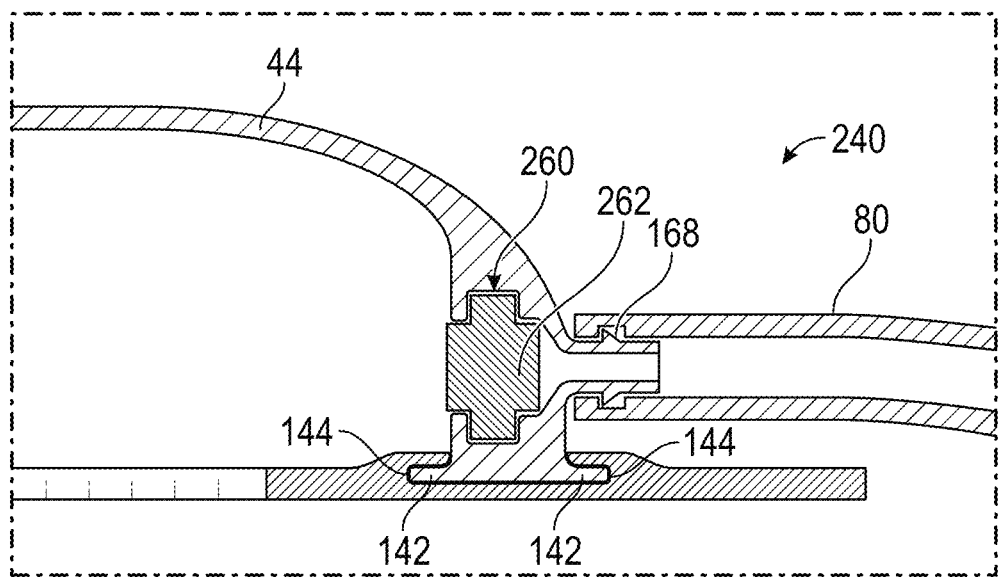
FIG. 7 is a side section view of an alternative primary collection element having an anti-backflow device of a different configuration.

In another implementation, a primary collection element 240 as shown in FIG. 7 is similar to the primary collection element 140, but it has an anti-backflow device 260 that is formed as a check valve or another similar type of valve that can be cast into the primary collection element 240 during manufacture or otherwise formed with it, or inserted into a space reserved for the anti-backflow device 260.

In still other implementations, the anti-backflow device or a portion thereof may be formed as one piece with one or more of the walls of the device, such as the wall 40. The anti-backflow device 260 may be formed of the same material(s) as the primary collection element 240, or of different material(s).

Figure 8:
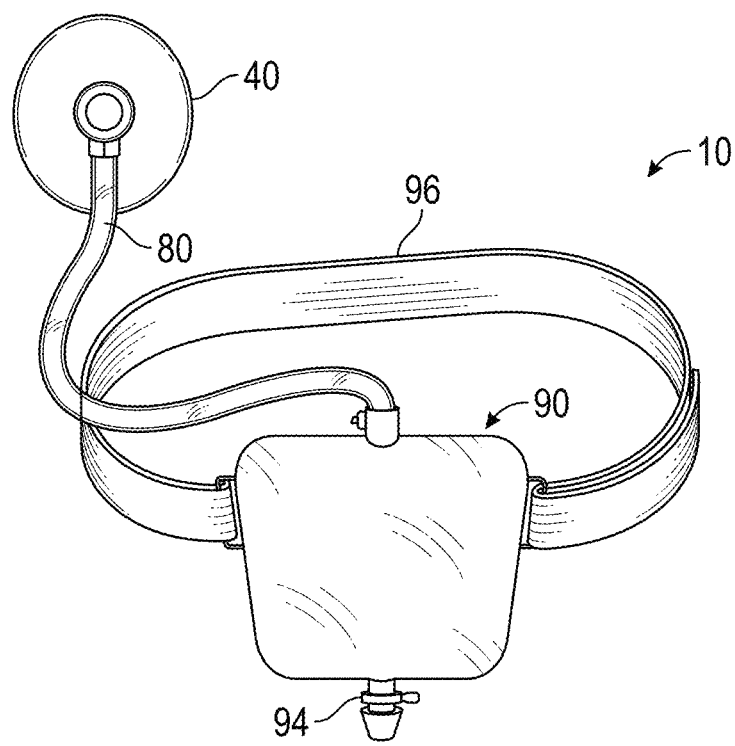
FIG. 8 is a perspective view of the urine collection device showing the secondary collection element configured for wearing on a belt.

FIG. 8 is an illustration of the urine collection device 10 with the secondary collection element 90 configured for wearing on a belt 96. The belt 96 is intended for positioning around the waist (or belt line) of the user, and at a height below the stoma (when the user is upright). In this way, the flow of urine from the primary collection element 40 through the drain tube 80 and to the secondary collection element 90 is generally downward and thus assisted by gravity.

Figure 9:
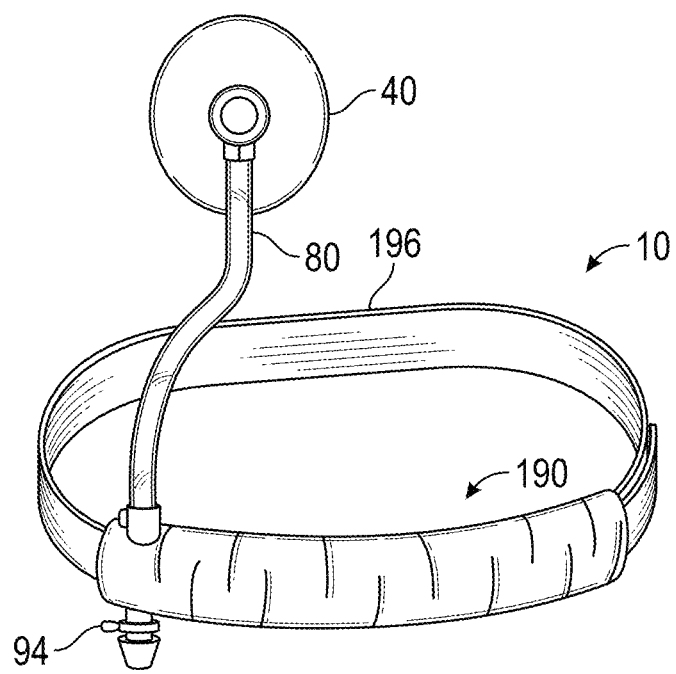
FIG. 9 is a perspective view of the urine collection device showing an alternative secondary collection element configured as a tube-shaped container that follows the contour of a belt.
Figure 10:
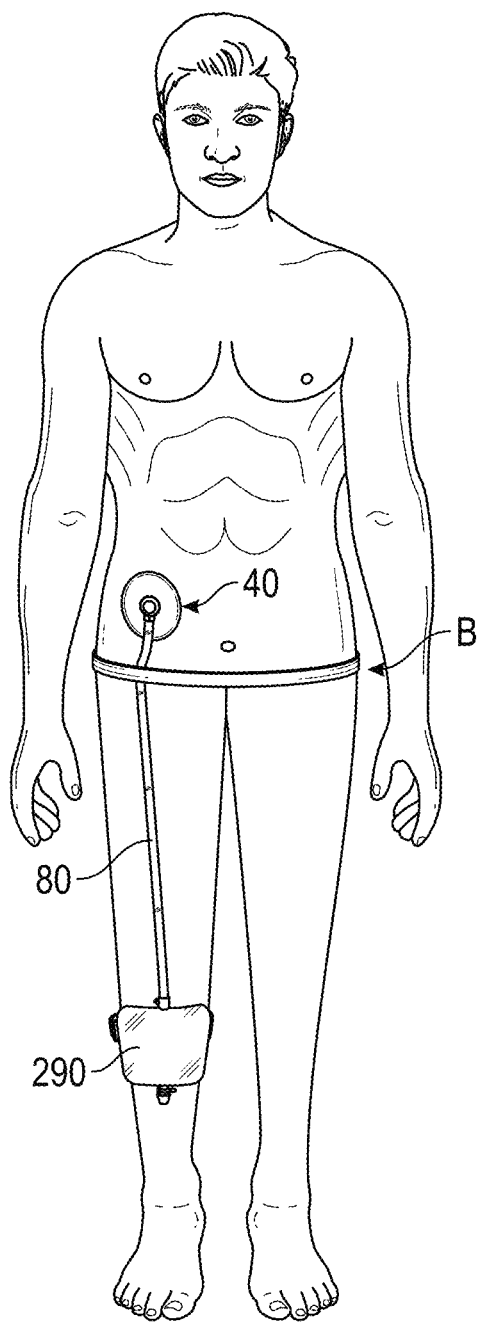
FIG. 10 is a perspective view of a user wearing the urine collection device, with the primary collection device mounted to the surround a stoma in the midsection and the secondary collection device positioned below the beltline, such as in a leg bag configuration that is attached to a leg of the user as shown.

FIG. 9 is an illustration of a secondary collection element 190 that is also belt-worn, but is shaped to have a tube-like configuration that follows the contour of the belt and the user's waist to provide greater comfort and ease of positioning, particularly in seated positions. FIG. 10 is an illustration of a secondary collection element 290 that is configured to be mounted to a leg of the user (which is also below the belt line when the user is upright). Although the secondary collection element 290 is shown mounted to the lower leg, it could also be mounted to the upper leg.

Figure 11A:
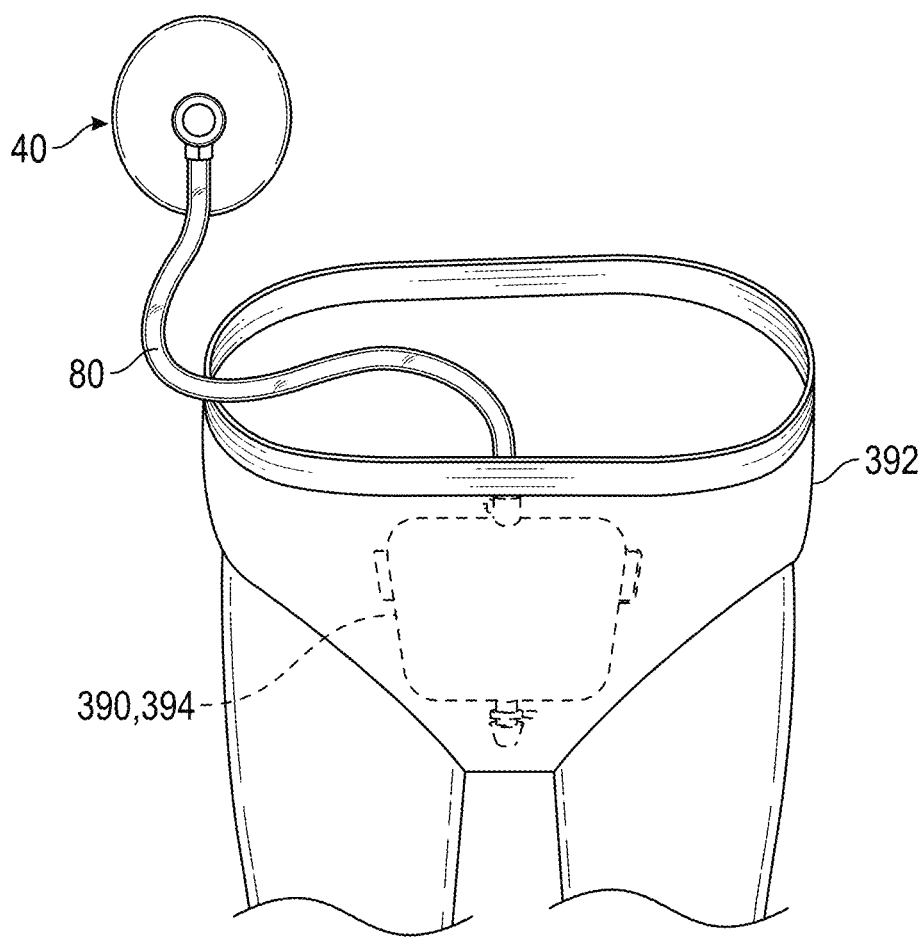
FIG. 11A is a perspective view of the urine collection device in which an alternative secondary collection element is configured to be worn under or incorporated into underwear or another undergarment or garment.
Figure 11B:
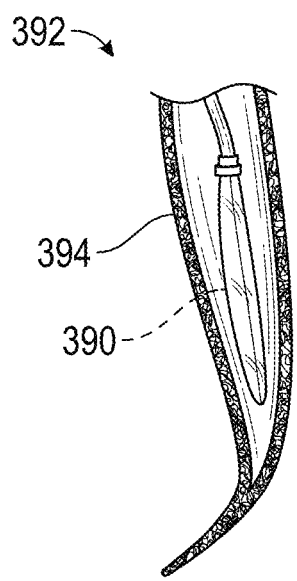
FIG. 11B is a side elevation section view of the urine collection device of FIG. 10 showing the secondary collection element positioned within the underwear.

FIGS. 11A and 11B show a secondary collection element 390 configured for wearing in conjunction with a garment, such as underwear 392 or another type of garment. The secondary collection element 390 may be simply inserted into the underwear 392, or the underwear may be fitted with an internal or external pocket. In the illustrated implementation, an internal pocket 394 within the underwear 392 is shaped to receive the secondary collection element 390.

In the above implementations, the volumetric capacity of the primary collection element can be smaller than the volumetric capacities of conventional bags or pouches. A smaller primary collection element is lower in weight and exerts less pressure on the adhesive and skin.

Also, any of the described anti-backflow devices can be configured to be replaceable, such as by removing a used or damaged anti-backflow device and inserted a replacement, particularly in implementations where the primary collection device is formed of a relatively flexible material.

In some implementations, the primary collection device can be cleaned for reuse.

In view of the many possible embodiments to which the principles of the disclosed invention may be applied, it should be recognized that the illustrated embodiments are only preferred examples and should not be taken as limiting the scope of protection. Rather, the scope of protection is defined by the following claims. I therefore claim as my invention all that comes within the scope and spirit of these claims.

I claim:

1. A urine collection device for a person, comprising:
a primary collection element shaped to surround a stoma formed in the person's abdomen;
an outlet opening in the primary collection element via which urine received in the primary collection element through the stoma exits the primary collection element;
a drain tube connected to the outlet opening in the primary collection element and extending distally from the primary collection element, the drain tube draining urine from the primary collection element;
an anti-backflow device positioned at the outlet opening of the primary collection element or within the primary collection element, the anti-backflow device restricting urine from backflowing from the drain tube into the primary collection element; and a secondary collection element connected to the distal end of the drain tube to collect the urine draining from the drain tube, wherein the secondary collection element is configured for coupling to the person at a location spaced apart from the primary collection element.

2. The urine collection device of claim 1, wherein the secondary collection element is configured for coupling to the person below a beltline of the person.

3. The urine collection device of claim 1, wherein the outlet opening in the primary collection element comprises a protruding spout.

4. The urine collection device of claim 1, wherein the anti-backflow device is positioned in the primary collection element.

5. The urine collection device of claim 1, wherein the anti-backflow device is positioned in the outlet opening of the primary collection element.

6. The urine collection device of claim 1, wherein the anti-backflow device is a barbed check valve installed in the primary collection element with a barb fitting protruding through the outlet opening and connected to the drain tube.

7. The urine collection device of claim 1, wherein the anti-backflow device comprises a Luer fitting.

8. The urine collection device of claim 1, wherein the anti-backflow device comprises a duckbill-type member formed of a flexible material.

9. The urine collection device of claim 1, wherein the primary collection element is configured to be adhesively coupled to the person's skin.

10. The urine collection device of claim 1, wherein the secondary collection element is shaped to be suspended from a belt worn by the person, the belt being fitted for wearing adjacent the beltline.

11. A urine collection device for a person, comprising:
a primary collection element shaped to surround a stoma formed in the person's abdomen, the primary collection element having a base, a wall extending from the base and a primary collection volume defined by at least the base and the wall, further comprising a flange extending outwardly from the base and configured for adhesive attachment to the person's skin, and wherein the primary collection element is configured to receive urine from the body opening into the primary collection volume and convey the urine out of the primary collection volume in a first flow direction through an outlet opening in the wall;
an anti-backflow device positioned at the outlet opening in the wall or within the primary collection element;
a drain tube connected to the outlet opening in the primary collection element and extending distally from the primary collection element, the drain tube having a working length that extends at least as long as a distance from the body opening in the person's abdomen to a desired secondary collection element location below the person's beltline; and
a secondary collection element connected to the distal end of the drain tube to collect the urine draining from the drain tube, wherein the secondary collection member is configured for coupling to the person at the desired collection member location,
wherein the anti-backflow device is configured to restrict urine from backflowing into the primary collection volume in a second flow direction opposite the first flow direction and compromising the adhesive attachment between the base and the person's skin.

12. The urine collection device of claim 11, wherein the anti-backflow device prevents urine from backflowing into the primary collection volume and increasing pressure within the primary collection element.

13. The urine collection device of claim 11, wherein the anti-backflow device prevents urine from backflowing into the primary collection element and weakening the adhesive attachment between the flange and the person's skin.

14. The urine collection device of claim 11, wherein the anti-backflow device comprises at least one of a barbed fitting or a Leuer fitting.

15. The urine collection device of claim 11, wherein the anti-backflow device is positioned in the outlet opening in the wall.

16. The urine collection device of claim 11, wherein the anti-backflow device is a check valve inserted through the wall in the primary collection element with a barb fitting protruding through the outlet opening and connected to the drain tube.

17. The urine collection device of claim 11, wherein the anti-backflow device comprises a duckbill-type member formed of a flexible material.

18. The urine collection device of claim 11, wherein the collection member is shaped to be suspended from a belt worn by the person, the belt being fitted for wearing adjacent the beltline.

19. The urine collection device of claim 11, wherein the collection member is configured for being coupled to a leg of the person.

20. The urine collection device of claim 11, wherein the drain tube is sized for wearing under a belt or clothing waist band without being compressed by the belt or clothing waist band.

\* \* \* \* \*